United States Patent
Aeikens et al.

[11] Patent Number: 5,921,916
[45] Date of Patent: Jul. 13, 1999

[54] ENDOSCOPE UTILIZING A FIBER OPTIC HOLDING TUBE WITH A JACKET SLIT FOR LATERAL PLACEMENT OF THE FIBER OPTIC

[75] Inventors: Bernhard Aeikens, Bremen; Thorsten Ahrens, Seitingen-Oberflacht; Rüdiger Schwägler, Emmingen-Liptingen; Clemens Scholz, Freiburg, all of Germany

[73] Assignee: Ueth & Haug GmbH, Tuttlingen, Germany

[21] Appl. No.: 08/612,886

[22] PCT Filed: Jul. 6, 1995

[86] PCT No.: PCT/EP95/02623

§ 371 Date: Jun. 11, 1996

§ 102(e) Date: Jun. 11, 1996

[87] PCT Pub. No.: WO96/01589

PCT Pub. Date: Jan. 25, 1996

[30] Foreign Application Priority Data

Jul. 7, 1994 [DE] Germany ............... 44 23 529

[51] Int. Cl.⁶ .................................................. A61B 17/36
[52] U.S. Cl. .................. 600/108; 600/105; 600/129; 600/135; 600/182
[58] Field of Search ........................... 600/105, 106, 600/107, 108, 129, 135, 182, 160; 606/13, 15, 16

[56] References Cited

U.S. PATENT DOCUMENTS

| | | |
|---|---|---|
| 2,038,393 | 2/1936 | Wappler ............................. 600/105 |
| 2,888,017 | 9/1959 | Wallace ............................. 600/105 |
| 4,137,920 | 2/1979 | Bonnet .............................. 600/105 |
| 4,313,431 | 2/1982 | Frank ............................... 600/108 |
| 4,430,996 | 2/1984 | Bonnet .............................. 600/105 |
| 4,726,370 | 2/1988 | Karasawa ........................... 600/105 |
| 4,740,047 | 4/1988 | Abe ................................. 600/108 |
| 4,760,840 | 8/1988 | Fournier ........................... 600/108 |
| 4,870,952 | 10/1989 | Martinez .......................... 600/182 |
| 5,014,708 | 5/1991 | Hayashi ............................ 600/105 |
| 5,051,823 | 9/1991 | Cooper ............................. 600/108 |
| 5,136,676 | 8/1992 | Arnett .............................. 600/108 |
| 5,312,399 | 5/1994 | Hakky ............................... 606/15 |
| 5,421,323 | 6/1995 | Herrmann ......................... 600/108 |
| 5,428,699 | 6/1995 | Pon .................................. 600/108 |
| 5,509,917 | 4/1996 | Cecchetti .......................... 606/15 |

*Primary Examiner*—Gene Mancene
*Assistant Examiner*—Ira Hatton
*Attorney, Agent, or Firm*—Antonelli, Terry, Stout & Kraus, LLP

[57] ABSTRACT

An endoscope, in particular for applications in urology, has a hollow shaft (10), an optical viewing system (12) which can be inserted in the hollow shaft (10) and has a fiber-optic illumination system, an optical fiber (16) which can be introduced with the optical system (12) into the hollow shaft (10) and connected at its proximal end to an external laser source and is bent at its distal end away from the shaft axis. In order to allow irradiation of tissue lying closely packed around the hollow shaft, an indeformable holding tube (14) which is parallel to the optical system (12) and passes through the hollow shaft (10) is provided; this tube accommodates the optical fiber (16) and its distal end is bent at a fixed angle in relation to the shaft axis and accommodated entirely within the shaft cross-section. A spacer (36) with a radiation window (32) ensures that the tissue to be irradiated cannot lie next to the point (18) at which light emerges from the optical fiber (16).

35 Claims, 7 Drawing Sheets

ENDOSCOPE UTILIZING A FIBER OPTIC HOLDING TUBE WITH A JACKET SLIT FOR LATERAL PLACEMENT OF THE FIBER OPTIC

DESCRIPTION

The invention relates to an endoscope, especially for urological applications, comprising a hollow shaft, an optical viewing system which has a fiber optical source of illumination and which is positioned inside the hollow shaft, and an optical fiber which is preferably positioned inside the hollow shaft together with the optical viewing system, which is connected to an external laser light source at its proximal end and the distal end of which is bent away from the axis of the shaft.

During urological applications, the endoscope is initially inserted with its hollow shaft, which has a rounded mandrin at its distal end, through the urethra into the vicinity of the area of irradiation in the region of the prostata or the bladder. After the removal of the mandrin, the optical viewing system and the optical fiber are inserted into the hollow shaft from the outside. In order to enable an irradiation which is angled with respect to the axis of the shaft, it is hitherto known to bend the optical fiber at its distal end with respect to the axis of the shaft with the aid of a suitable lever mechanism of the type of an Albarrans's lever. It is then possible to direct the laser beam in different directions during the surgery. In order to avoid damaging the optical fiber, a predetermined, relatively large radius of bending of the optical fiber may not be fallen below. In keeping with this, the optical fiber and a part of the lever mechanism protrude over jacket of the shaft in the angled state, so that an operation when tissue is directly adjacent to the shaft, as for instance in the region of the urethra or prostata, is not possible. In order to avoid this disadvantage, irradiation techniques employing reflective or refractive laser beam deflection have been suggested. The mirror- and prisma-arrangements necessary for these techniques are technically complicated and sensitive with respect to contamination, though, and they require a higher power density due to an unavoidable defocussing of the laser beam. Urological irradiations of this type are hitherto performed under a general anaesthesia of the patient.

Based on this, it is the object of the invention to develop an endoscope of the type desribed above, which enables an irradiation also of tissue which is in close contact with the shaft.

In order to solve this object, the combination of features stated in patent claim 1 is suggested. Advantageous embodiments and further developments of the invention result from the dependent claims.

The solution according to the invention is based on the idea that the optical fiber, which is composed of a fiber core and at least two cover layers, can be bent also about a relatively small radius of bending, if it is supported in the region of the bend sufficiently rigidly with respect to unwanted multiple bending. In order to achieve this, there is suggested according to the invention a rigid holding tube for accepting the optical fiber, which extends through the hollow shaft in parallel to the optical viewing system and the distal end of which is bent away from the axis of the hollow shaft by a fixed angle of 10° to 110° and positioned fully within the cross section of the hollow shaft. In this, the radius of bending of the holding tube is substantially smaller than the average diameter of the shaft, preferably one quarter to one half of the average diameter of the shaft. Advantageously, the optical fiber protrudes with its free distal end over the free end of the holding tube within the cross section of the hollow shaft.

In view of the small radius of bending of the holding tube in the region of the bend, the optical fiber cannot simply be pushed through the tube, since the deformation of the fiber together with the bend would certainly lead to a braking of the fiber. Advantageously, provisions are therefore made to lead the optical fiber through the tight bend within the holding tube without braking the fiber. To this end, the holding tube has a jacket slit for laterally inserting the end of the optical fiber at least in the region of its bent distal end. In this, the jacket slit may extend parallel to the axis from the distal end over a distance in the straight part of the holding tube. The important thing is that the flexible optical fiber is held in its bent shape by the wall of the holding tube in the region of the bend as well as at its free end. It is then of advantage that the jacket slit is proximally open at least in the vicinity of the free bent end of the holding tube. In a one-piece holding tube the jacket slit advantageously has such a helical shape, so that it is open in the distal and/or lateral direction at the root of the bend and in the proximal direction in the vicinity of the free end of the holding tube. At the same time, the part of the holding tube which has a closed jacket and is aligned axially should have an axial passage opening for the optical fiber, the passage opening being formed by the helical and laterally bent jacket slit. With these measures it is achieved that the holding tube is opened at its distal end in the region of the bend while forming the jacket slit so that an opening for the straight passage of the optical fiber remains free in the axial direction, and that it has a helical shape in the bent part such that the optical fiber is distally supported. During the insertion of the optical fiber through the helical jacket slit the fiber has to be bent slightly more than in its final state, so that it can catch in the holding tube in the region of the jacket slit by the action of its elasticity.

In a further embodiment, the jacket slit extends straight past the bend toward the free distal end. In this case, the holding tube advantageously incorporates a clamping member which pushes the optical fiber into the jacket slit and also bends the end of the optical fiber. The clamping member may then be formed to be a clamping shell which is bent at its distal end, movable on the holding tube in an axially parallel direction, and which has a slit opening which is complementary to the jacket slit of the holding tube or which overlaps or projects into the jacket slit, the clamping member being engageable in the holding tube in its end position.

In a further embodiment, the holding tube has a closed ring which delimits the jacket slit at the distal end of the holding tube. The optical fiber is first pushed through the axially aligned part of the holding tube with a certain projecting length. The projecting length is then bent and inserted through the closed ring. The fiber loop remaining in the region of the jacket slit is stretched tight by retracting the optical fiber through the axially aligned part and brought into an adjoining position at the bend of the holding tube.

In a further preferred embodiment of the invention, the holding tube is aligned parallel with respect to the optical viewing system within the hollow shaft and is bent toward the optical path of the optical viewing system at its distal end. The optical viewing system advantageously has an observation angle which is directed slanted with respect to the axis of the shaft in the direction of the area of irradiation, wherein the angle of bending of the holding tube and of the optical fiber with respect to the axis of the shaft is two to nine times greater than the angle of observation of the optical viewing system. With this measure it is achieved that the area of irradiation can be viewed from an angle within the limit of movement of the holding tube by means of the optical viewing system.

According to a further preferred embodiment of the invention, the hollow shaft has an oval cross section, wherein the axes of the optical viewing system and of the holding tube penetrate the long principal axis of the oval cross section of the hollow shaft. In this, the optical viewing system is positioned generally in the center of the hollow shaft and that the holding tube is positioned eccentrically and preferably nonrotatably in the hollow shaft.

A further improvement in this respect is achieved when the hollow shaft has an opening in the vicinity of its distal end, which is open in the direction of the bend of the holding tube, which extends to the distal end and which is preferably limited by a beak-like shaft tip. Furthermore, it is advantageous especially for the irradiation of tight regions of tissue when the free bent end of the holding tube is laterally enclosed by a distance piece. The distance piece may simultaneously be formed to be a window defining the area of irradiation, for instance in the shape of a wire loop. Advantageously, the wire loop is positioned movably within the opening in the hollow shaft and is preferably rigidly connected to the hollow shaft. The distal end of the wire loop may be bent against and affixed to the distal end of the shaft in a clip-like manner.

The effect of the laser radiation is determined by the contact or non-contact of the end of the fiber with the tissue: In the contact mode preferably cutting or preparing is performed, whereby the effect of coagulation at the seam of the preparation is reduced. In the non-contact mode coagulation is preferably performed with a reduced power density of the laser radiation, and with a high power density tissue can be vaporized while at the same time bleeding at the work site is stopped. The application of the distance piece depends on the desired effect on the tissue.

In a further embodiment of the invention the holding tube consists of a pliable metallic alloy, preferably of a nickel-titanium alloy. It is then possible to bend the holding tube together with the inserted optical fiber at its distal end in the desired manner, without having to insert the distal end of the fiber into the holding tube afterwards.

A further advantage of the invention is that the optical fiber may be shortened by the bent part at its distal end after an irradiation and then be inserted into the holding tube again for a further irradiation.

In order to enable an irradiation of a predetermined area which is accessible by the optical viewing system, the holding tube can be movable to-and-fro in a limited way relative to the optical viewing system in the direction of the axis of the hollow shaft by means of a proximal actuating mechanism. The actuating mechanism advantageously has a holder which carries the optical viewing system and is removably connected to the proximal end of the hollow shaft, and a slider which is movable relative to the holder parallel to the axis of the hollow shaft against the force of a spring and carries the holding tube. Since the optical fiber is very sensitive, it may frequently occur that a replacement during surgery becomes necessary. For such a replacement, the complete holding tube together with the optical fiber is advantageously exchanged. Since the holding tube is bent at its distal end, it cannot simply be pulled axially away from the optical tube of the optical viewing system. An advantageous embodiment of the invention therefore provides that the holder has an axial guide for the holding tube, which is formed by a guide jaw which is connected to the holder and which carries the optical viewing system and by a guide jaw which is separated from the holding tube in an axial parting plane of the holding tube and movable in a limited way along the holder transverse to the parting plane. By lifting the movable guide jaw a sufficiently large gap is created, through which the holding tube with its bent end fits during the replacement. During this operation, the guide jaws are pressed against each other while leaving free a small guide opening for the holding tube. To this end, the guide jaws have partially conical shoulders which complement each other to form a closed outer cone, are insertable into an inner cone of the hollow shaft, are clampable in this preferably by way of a bayonet catch in a fluid-tight manner, and can be pressed against each other at their parting plane.

In order to further improve the guiding properties an axial guide for the holding tube is additionally positioned at the enclosing surface of the optical tube, the axial guide being radially open-edged, so that the holding tube may there be laterally insertable or removable.

According to a preferred embodiment of the invention, the holding tube has a radially protruding adjusting member rigidly positioned at its proximal end, and the slider has an axially continuous, radially accessible slotted receiving means for the holding tube, the slotted receiving means having a pocket which retains the adjusting member in an axially form-fitting manner. In order to be able to laterally align the optical fiber which protrudes over the distal end of the holding tube, it is advantageous that the adjusting member is limitedly pivotable in the pocket together with the holding tube about the axis of the holding tube by way of a positioning mechanism which is positioned on the slider.

With these measures it is possible to easily replace the holding tubes which are provided with optical fibers during surgery. In order to do this, the holder only has to be removed from the hollow shaft and exchanged for a prepared holder, before this is re-inserted into the hollow shaft. In order to make this operation even simpler, it is further advantageous to use optical fibers which have a precision plug-type connector at their proximal end which axially protrudes over the holding tube for the connection to a socket which leads to the laser light source by way of a mother fiber. The result is a two-part fiber system, consisting of a short, disposable patient fiber, which comes into contact with the patient, and a durable, reusable mother fiber.

Laser endoscopes of this type are especially well suited in urology for transurethral resection of the prostata and the bladder. Further applications are in otolaryngology endoscopic nasal and paranasal surgery, polypectomy, endoscopic laryngopharyngeal surgery, in the field of gynaecology hysteroscopic septum dissection, hysteroscopic myomectomy, hysteroscopic cornual polypectomy, endoscopic capsulotomy, endometrial ablation, and in surgery adhesiolysis, bloodless preparation, coagulation.

The endoscope as described above may in principle also be fitted with an applicator tube for laser induced thermotherapy. Then a holding tube having a cannular bevel at its distal end is to be used. Further, a holder-connected locking member which acts on the proximal end of the optical fiber has to be provided, which permits to leave the optical fiber in the tissue to be irradiated, when the cannula is retracted.

Furthermore, the endoscope can easily be fitted with an applicator tube for local anaesthesia in the area to be irradiated. To this end, the holding tube is exchanged for an application tube which is subjectable under pressure to a fluid, preferably an anaesthetic, and which has a nozzle at its distal end. The nozzle may formed to be a saphire nozzle having a very small cross section in the range of 50 to 300 μm, through which the anaesthetic may be infiltrated into the tissue at high speed. The distal end of the application tube is advantageously bent with respect to the axis of the hollow shaft by a fixed angle of 10° to 110° and is fully located inside the cross section of the hollow shaft. These measures provide the surgeon with new possibilities of local anaesthesia in body cavities under optical supervision.

In the following, the invention is further described with the aid of embodiments schematically shown in the drawing, in which

FIG. 3a shows a partial side view of a laser endoscope having a movable distance piece in a representation corresponding to FIG. 2a;

FIG. 3b shows a bottom view of the endoscope of FIG. 3a;

FIG. 14a and b show a side view and a front face view of the open-edged axial guide, which is positioned at the distal end of the optical tube, for the holding tube;

FIG. 15a and b show a top view and a vertical section of the slider of the actuating mechanism with the inserted holding tube.

Figure 1:
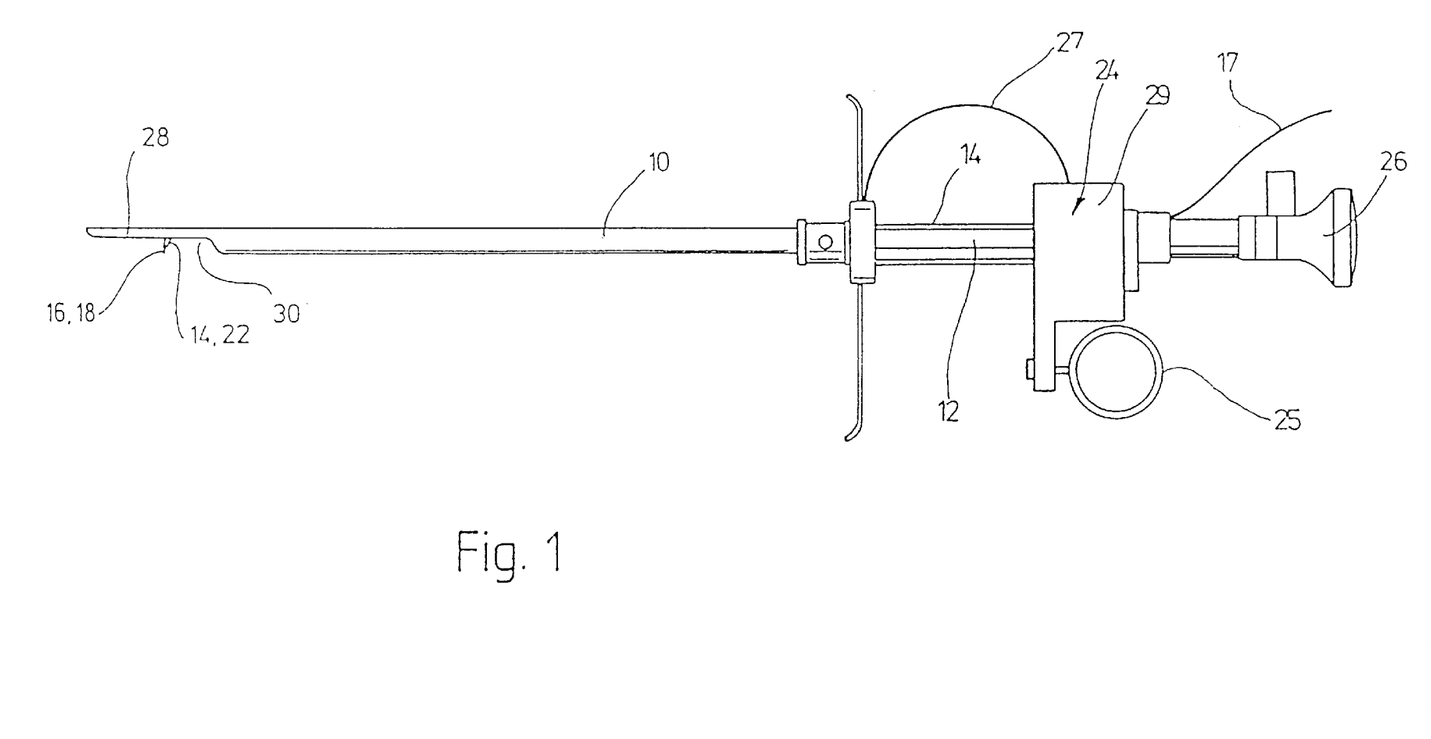
FIG. 1 shows a side view of a laser endoscope.
Figure 11:
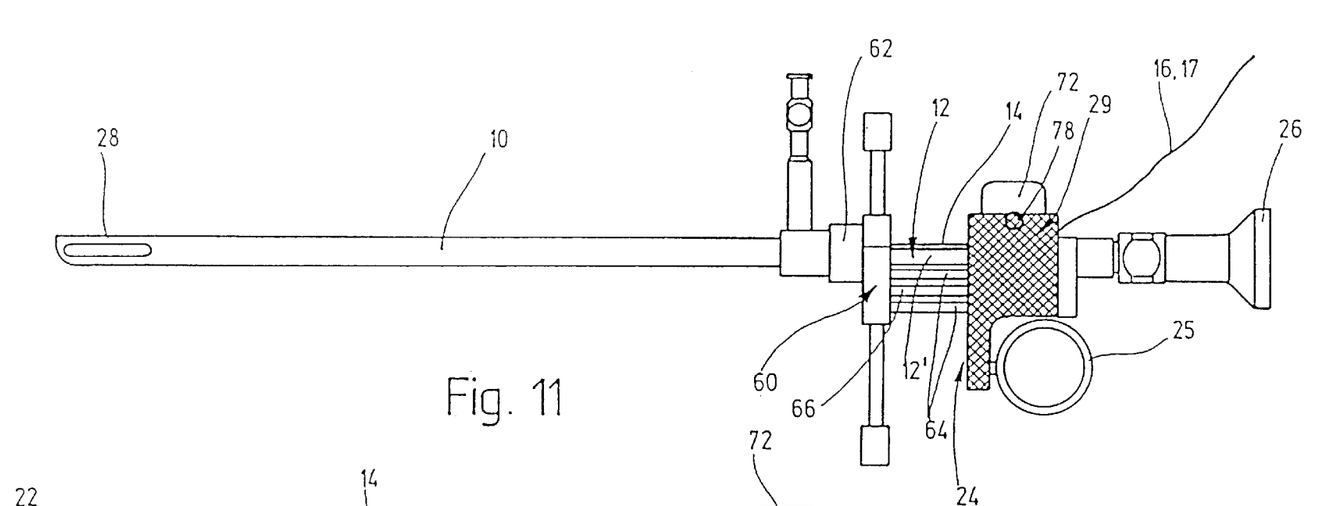
FIG. 11 shows a side view of an embodiment of a laser endoscope modified with respect to FIG. 1.

The laser endoscopes shown in FIG. 1 and 11 are to be used especially in urological applications. They comprise a hollow shaft 10 having an oval cross section, an optical viewing system 12 which is insertable into the hollow shaft 10 and which has a fiber optical source of illumination, as well as a holding tube 14 for an optical fiber 16, which is insertable into the hollow shaft together with the optical viewing system. The proximal end 17 of the optical fiber 16 can be connected to an external laser light source 19 via a plug-type connector 15 and a mother fiber 13, and is bent at its distal end 18 with respect to the axis of the shaft in the direction of the optical viewing system by approximately 90° in the embodiments shown. The flexible optical fiber is held at a bend 20 of the rigid holding tube 14 in the region of its distal end 18 such that it protrudes with its free end within the cross section of the shaft over the free end 22 of the holding tube. In order to enable an irradiation within a predetermined area of treatment which can be viewed by the optical viewing system, the holding tube 14 is movable to-and-fro with respect to the optical viewing system 12 in the direction of the axis of the shaft with the aid of a proximal actuating mechanism 24. The actuating mechanism 24 therefore has a slider 29 which is movable in a direction parallel to the axis with respect to the hollow shaft 10 by means of a finger grip 25 against the force of a spring 27, the slider 29 being unmovably connectable to the holding tube 14. The angle of observation of the optical viewing system is chosen such that the whole area of treatment can be viewed within the limits of movement of the holding tube 14 while the hollow shaft 10 is held at a fixed position. The angle of observation with respect to the axis of the shaft is correspondingly slightly smaller than the angle of bending of the holding tube 14 and the optical fiber 16. The eyepiece 26 of the optical viewing system 12 is positioned in the vicinity of the actuating mechanism at the proximal end of the hollow shaft 10.

The optical tube 12' containing the optical viewing system is rigidly connected to the holder 60, which can be removably coupled to the hollow shaft 10 by means of a bayonet catch 62. The holder 60 supports the slider 29 of the actuating mechanism 24, which is movable in an axial direction along the holder-connected guide rails 64 against the force of the spring 27. In the embodiment shown in FIG. 11 the spring is positioned hidden in a spring cylinder 66.

Figures 14A, 14B, 15A, 15B:
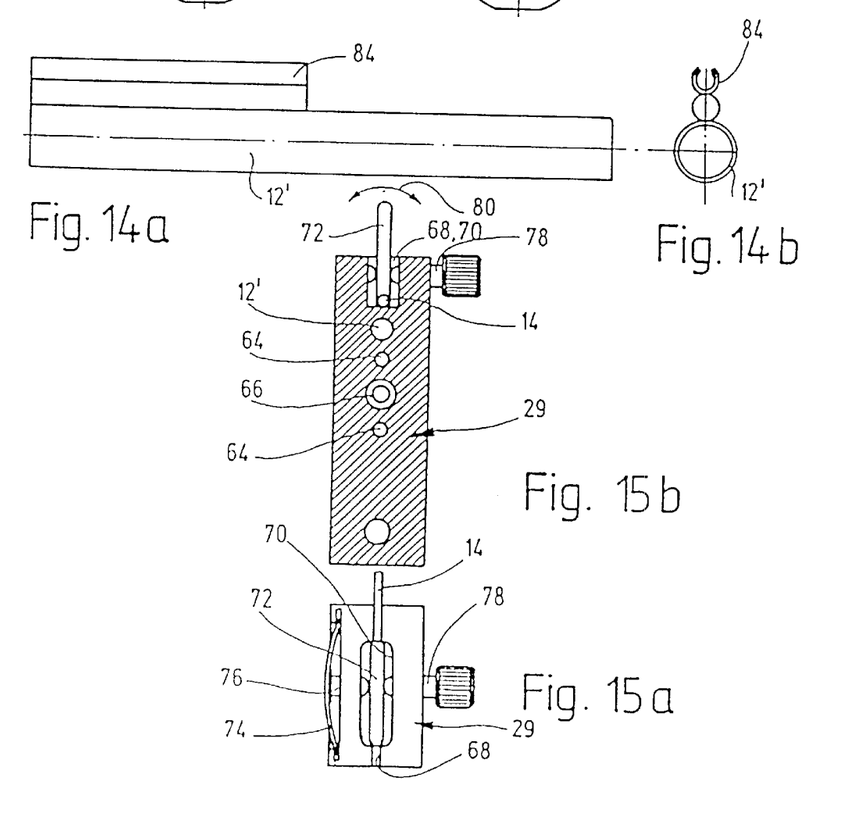

The holding tube 14 can be connected unmovably on the slider 29. To this end, the slider 29 has an axially continuous slotted receiving means 68 for the holding tube 14, which is accessible from above and which broadens in its middle region to form a pocket 70, into which a plate-shaped adjusting member 72 engages axially form-fitting and protruding over the top, the adjusting member 72 being rigidly connected to the holding tube 14 and protruding radially over this. A tappet 76 tensioned by a leaf spring 74 and a screw-type bolt 78 each abut one broad side face of the adjusting member 72 above the holding tube 14. By the actuation of the bolt 78 it is possible to limitedly swivel the adjusting member 72, and therefore also the holding tube 14 rigidly connected to this, about the axis of the holding tube in the direction of the double arrow 80. In this manner the angular position of the bent distal end 18 of the holding tube can be adjusted with respect to the hollow shaft 10. The bolt 78 and the spring tappet 76 at the same time have a holding function for the adjusting member 72 and the holding tube 14.

Figure 13A:
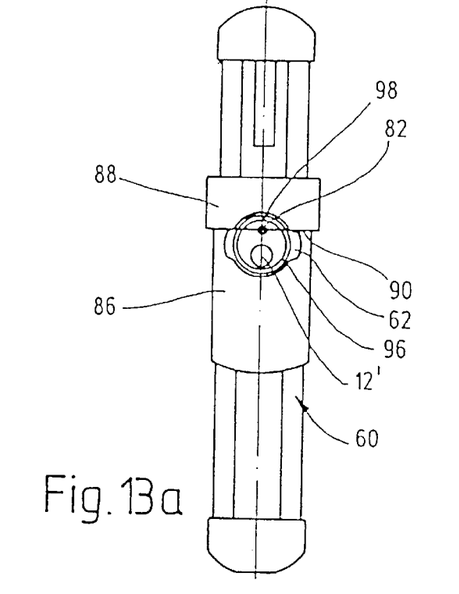
FIG. 13a and b show a front face view of the holder according to FIG. 11 with the hollow shaft removed and with closed and opened guide jaws for the holding tube.
Figure 13B:
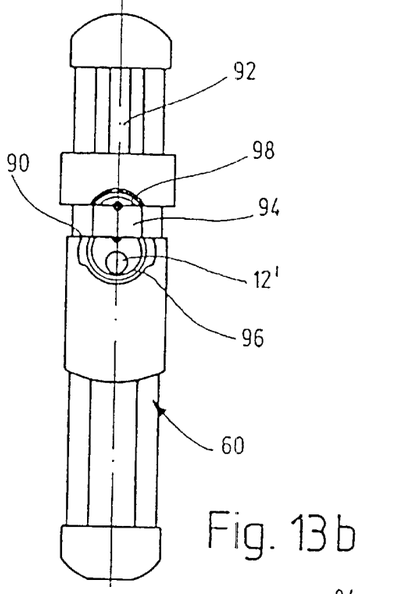

The holding tube 14 is additionally axially guided in an axial guide 82 of the holder 60 and in an axial guide, which is formed to be an open-edged catch bushing 84, in the region of the distal end of the optical tube 12'. In order to be able to undo the holding tube 14 with its bent distal end 22 from the axial guides 82, 84 and remove it from the slider 29, the axial guide 82 is separated into two parts. It has a guide jaw 86 which is connected to the slider and a laterally movable guide jaw 88 which abuts this (FIG. 13a) in an axial parting plane 90 and can be lifted off from this (FIG. 13b). During the lifting-off of the guide jaw 88 this abuts the stop 92 and opens a gap 94, through which the holding tube 14 with its bent distal end fits. The guide jaws 86, 88 have partially conical shoulders 96, 98 which complement each other to form a closed outer cone when the guide jaws lie flush against each other (FIG. 13a). The outer cone serves the tight coupling to the hollow shaft 10, which to this end has at its proximal end in the region of the bayonet catch 62 an complementary inner cone which accepts the outer cone.

Figure 2A:
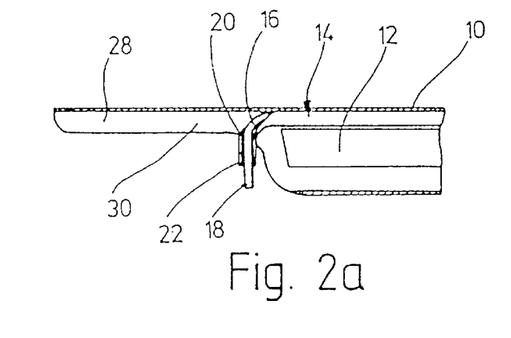
FIG. 2a and b show an enlarged section of the distal end of the laser endoscope according to FIG. 1, the hollow shaft being cut open, in two end positions of the holding tube with the optical fiber.
Figure 2B:
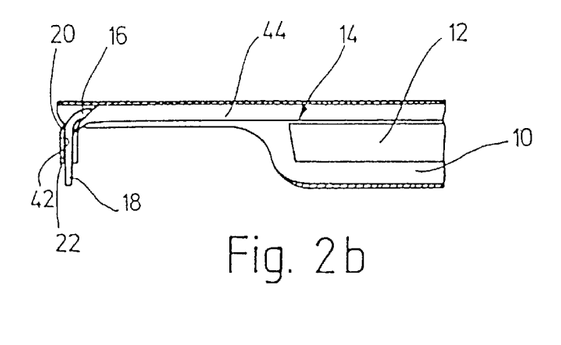
Figures 3A, 3B:
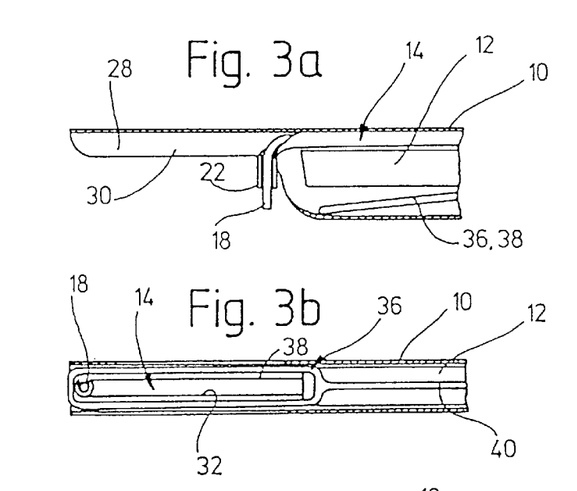
Figure 3C:
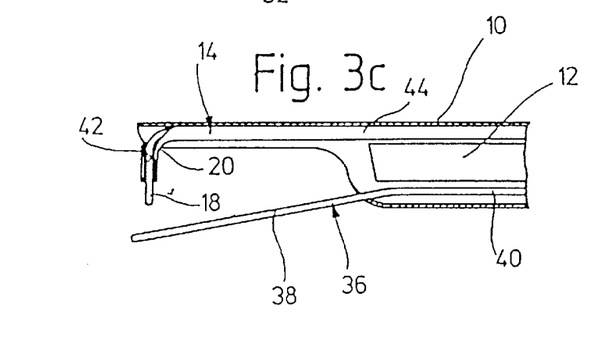
FIG. 3c shows a representation corresponding to FIG. 3a with the holding tube and distance piece extended.
Figure 3D:
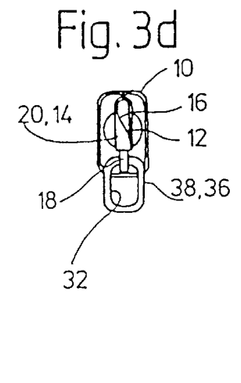
FIG. 3d shows a front face view of the laser endoscope of FIG. 3a to 3c.
Figure 4:
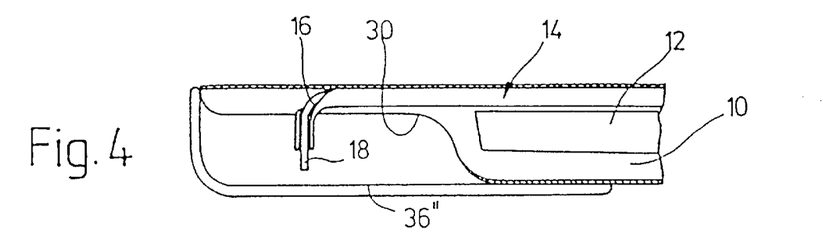
FIG. 4 shows a further embodiment of a laser endoscope in a partial side view with a cut open hollow shaft.
Figure 5A:
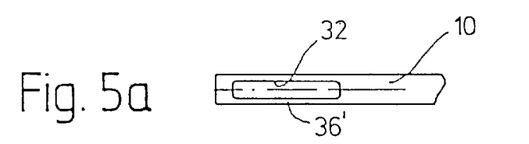
FIG. 5a to c show the distal end of a hollow shaft having three windows according to FIG. 11 in two side views and a front face view.
Figure 5B:
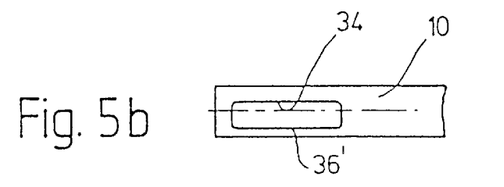
Figure 5C:
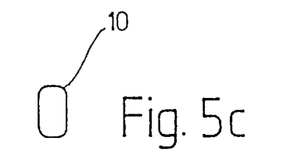
Figure 6A:
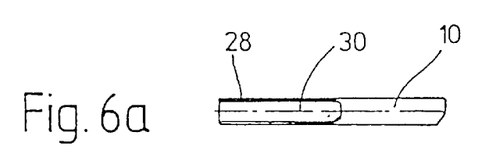
FIG. 6a to c show the distal end of a hollow shaft having a beak-like, open-edged window opening in two side views and a front face view.
Figures 6B, 6C:
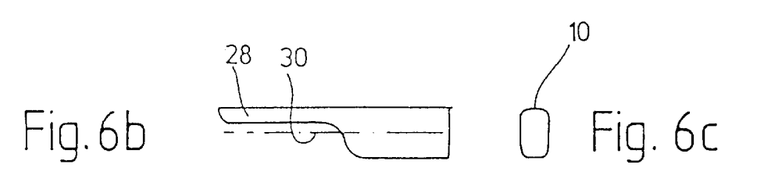
Figure 7A:
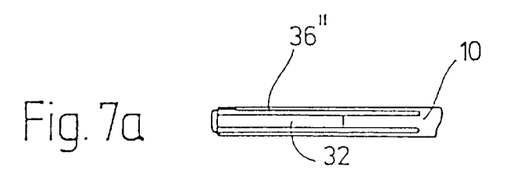
FIG. 7a to c show the distal end of a hollow shaft having a wire loop window in two side views and a front face view.
Figures 7B, 7C:
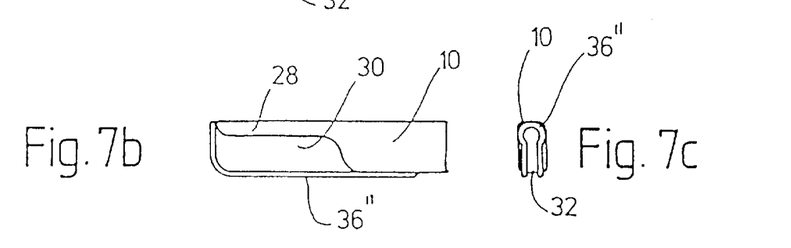

The bent distal end of the holding tube 14 and of the optical fiber 16 is located in a part 28 of the hollow shaft 10 which is open toward the area of irradiation. The open part 28 of the hollow shaft 10 may either be formed to have a beak-like shape and have a boundary opening 30 (FIG. 2a and b, 6a to c), or to have lateral window openings 32, 34 in the hollow shaft 10 (FIG. 5a to c, 4, 7a to c, 11). With the unilateral boundary opening 30 according to FIG. 2a and b, 6a to c, it is possible for tissue adjacent to the hollow shaft 10 to come into contact with the distal end of the optical fiber. If this is found to be undesireable, there may additionally be provided a distance piece 36 which, in the sense of FIG. 3a to d, may also be movable within the hollow shaft 10 and used only when needed. The distance piece 36 has a wire loop 38 at this point, which delimits an irradiation window 32 for laser radiation exiting from the optical fiber 16 and which is led to the proximal end by way of a rearward actuating rod 40. In the embodiments shown in FIG. 3a to d, the wire loop 38 is bent slightly toward the outside with respect to the actuating rod 40 at its distal end. The wire loop 38 also aids the orientation of the surgeon when viewing the area of irradiation.

The same also holds for the window arrangements 32, 34 at the distal end of the hollow shaft 10, wherein the edges 36', 36'' of the windows simultaneously fulfill the function of distance pieces in the embodiments shown in FIG. 5a to c, 7a to c, and 11. In the case of the FIG. 5a to c and 11 the windows 32, 34 are punched out of the wall of the hollow shaft 10, while in the case of the FIG. 7a to c they are formed by a wire frame 36'' which is soldered on in the region of the beak-like end of the hollow shaft 10 and which is bent at its front side.

In order to avoid a sticking of tissue to the distance piece, the distance piece may be provided with a non-stick coating consisting e.g. of polyfluorine tetraethylene (PTFE), titanium nitride or titanium carbon nitride.

Figure 8A:
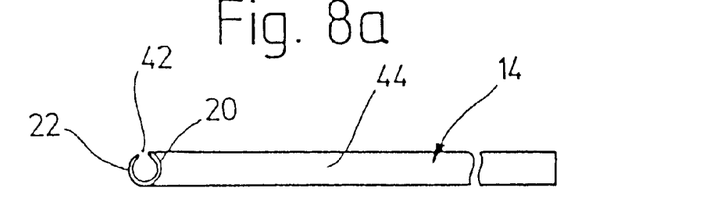
FIG. 8a to c show a one-piece holding tube for an optical fiber having a bent distal end and a helical jacket slit in two side views and a front face view.
Figure 8B:
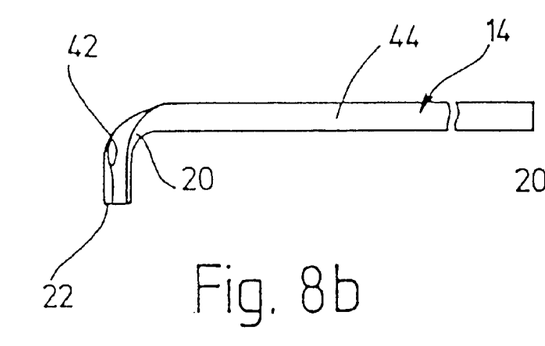
Figure 8C:
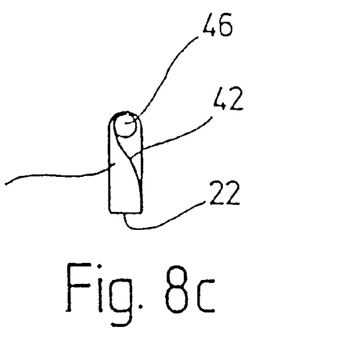

The radius of bending of the holding tube 14 in the region of the bend 20 is much smaller than the average diameter of the shaft under the present conditions. Accordingly, the optical fiber cannot be simply pushed through the holding tube in the region of the bend, since the otherwise resulting deformation would certainly lead to a breaking of the fiber. In order to avoid this, special provisions are made in the embodiments of FIG. 8, 9, and 10, so that the optical fiber can be led through tight bend 20 of the holding tube 10 without breaking. In all instances the holding tube 14 has a jacket slit 42 for laterally inserting the optical fiber 16 in the region of its distal end 18. In order for the optical fiber 16 to be sufficiently held in its bent region as well as at its free end 18 by the wall of the holding tube in its bent shape, the one-part holding tube 14 shown in FIG. 8a to c has a helical shape, which is open in the distal and lateral direction in the region of the root 44 of the bend and in the proximal direction in the vicinity of the free end 22. At the same time, the part 44 of the holding tube 14 which has a closed jacket and is aligned axially has an axial passage opening 46 for the optical fiber 16, the passage opening being formed by the helical and laterally bent jacket slit 42. The optical fiber 16 is first inserted through the straight part 44 starting at the proximal end so that its free distal end passes straight through the opening 46. The end protruding over the opening 46 is then bent in the direction of the bend 20 of the holding tube and laterally inserted into the bend 20 of the holding tube 14 through the helical jacket slit 42 under the action of its own elasticity.

Figure 9A:
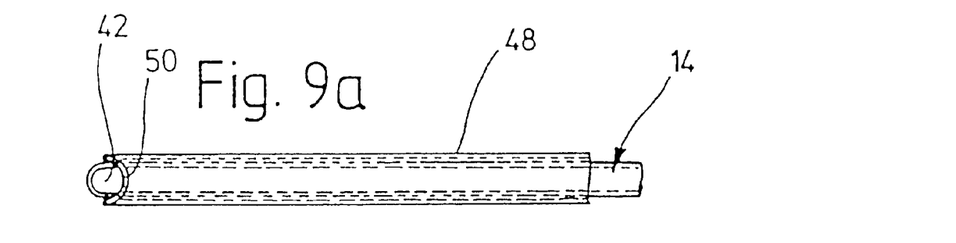
FIG. 9a and b show a two-piece holding tube having a bent distal end in two side views.
Figure 9B:
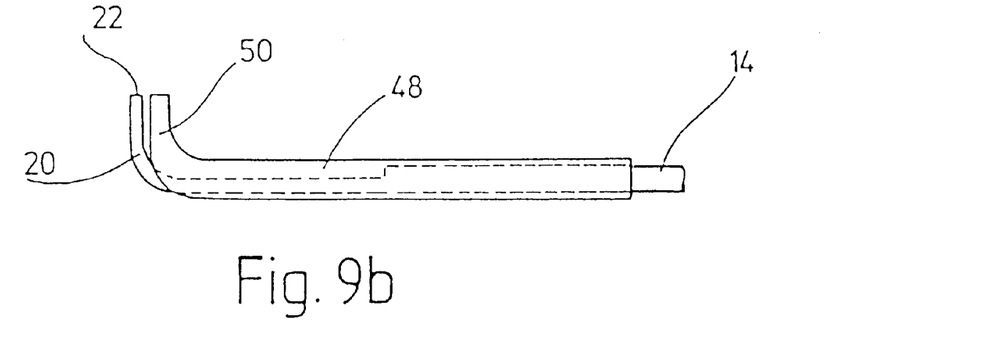
Figures 10A, 10B, 10D:
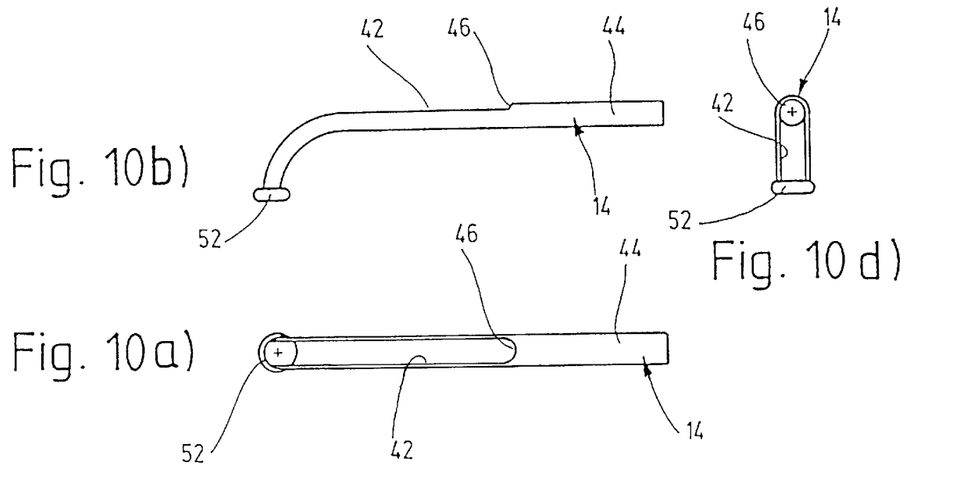
FIG. 10a to d show a one-piece holding tube having a jacket slit and an end ring in three side views and a front face view.
Figure 10C:
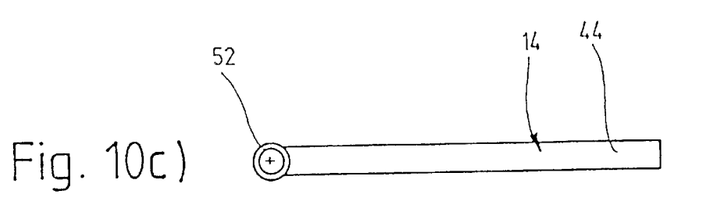

In the embodiments shown in FIG. 9a and b the jacket slit 42 is led in a straight line past the bend 20 toward the free distal end 22 of the holding tube 14. In this case, the holding tube 14 supports a clamping tube 48 which is movable in the direction of the bend 20 of the holding tube 14 with a bent open-edged clamping shell 50, and lockable in its end position in the holding tube. Thereby an optical fiber 16 led through the holding tube 14 can be held at the holding tube 14 by the clamping shell 50 by bending the end of the fiber into the jacket slit 42.

In the embodiments shown in FIG. 10a to d, the jacket slit 42 which overlaps the bend is delimited toward the free end by a closed ring 52. The optical fiber 16 is first inserted through the straight part 44 from the proximal end such that its free distal end passes straight through the opening 46. Then the end protruding over the opening 46 is bent and inserted through the closed ring 52. A fiber loop remaining between the opening 46 and the ring 52 is brought into contact with the bent region of the jacket slit 42 by retracting the optical fiber in the direction of the proximal end.

The holding tube 14 can be inserted into the hollow shaft complete with the optical fiber. The hollow shaft can remain in the urethra during this operation. In order to be able to quickly recognize a fracture of the optical fiber, the holding tube can be fitted with a thermoelement for measuring the temperature rise associated with laser radiation emanating from a fracture.

The preceding statements all relate to the use of the instrument as a laser endoscope, in which the holder 60 is fitted with a holding tube 14 which contains an optical fiber 16. The embodiment of the instrument shown in FIG. 11 in conjunction with FIG. 13 to 15 allows an easy exchange of the holding tube 14 which is fitted with an optical fiber 16. This is important since optical fibers are sensitive, and it cannot be excluded therefore that a replacement becomes necessary during surgery.

Figure 12:
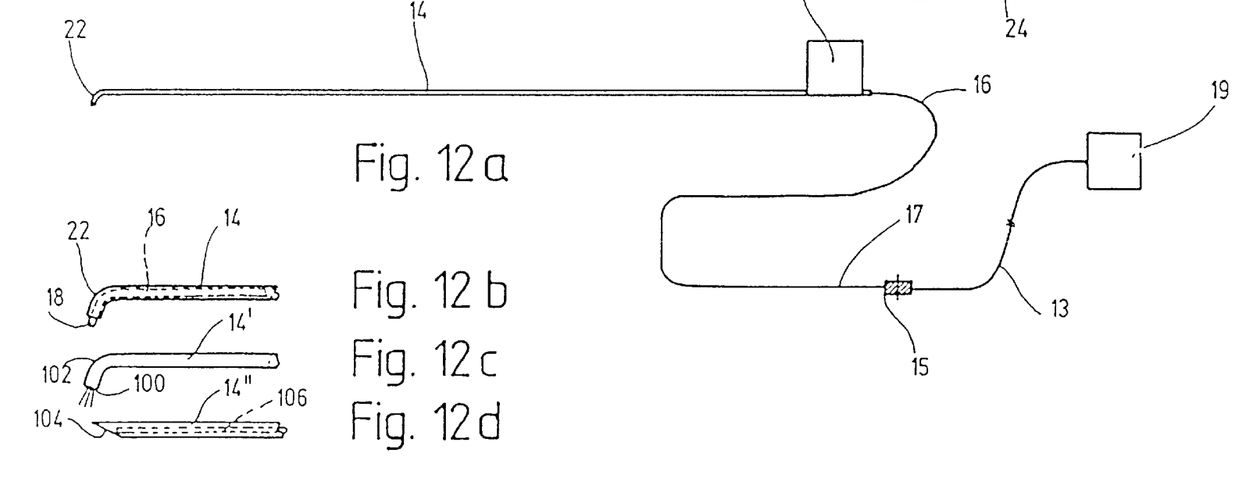
FIG. 12a shows a side view of a holding tube with an optical fiber.
FIG. 12b shows an enlarged section of FIG. 12a in the region of the distal end of the holding tube.
FIG. 12c shows the distal end of an application tube for local anaesthesia to be used with the instrument according to FIG. 11.
FIG. 12d shows the distal end of an application tube for laser-induced thermotherapy in a representation corresponding to FIG. 12b.

A further advantage of the instrument described is that the holding tube 14 fitted with an optical fiber 16 (FIG. 12a, b) can be fitted with an application tube 14' for local anaesthesia (FIG. 12c). The application tube 14' has a nozzle 100 at its distal end, and is connected to a high pressure pump with which a liquid anaesthetic can be infiltrated into the surrounding tissue through the application tube 14' under optical supervision. The application tube 14' is bent at its distal end 102 in a manner similar to the holding tube 14.

A further possible application of the instrument is laser-induced thermotherapy. To this end, an application tube 14'' is inserted into the instrument instead of the holding tube 14. This application tube is fitted with an optical fiber 106 which is subjectable to laser radiation, and which is not or only slightly bent at its distal end 104 and formed in the manner of a cannula. The application tube 14" is inserted into the tissue which is to be irradiated in a defined manner with the fiber 106 in a retracted position. The fiber may then be held at the irradiation site by way of a locking member (not shown) and the application tube 14" can be retracted using the actuating mechanism, before the optical fiber 106 is subjected to laser radiation.

For performing a combined therapy using laser radiation and high frequency current, the holding tube 14 and the holder 60 can be replaced by an alternative holder having a suitable high frequency electrode (loop, roller ball, cylinder roller), without removing the hollow shaft 10 from the patient.

In summary the following can be stated: The invention relates to a laser endoscope, especially for urological applications. The laser endoscope comprises a hollow shaft 10, an optical viewing system 12 which has a fiber optical source of illumination and which is positioned inside the hollow shaft 10, and an optical fiber 16 which is preferably positioned inside the hollow shaft 10 together with the optical viewing system 12, which is connected to an external laser light source 19 at its proximal end and the distal end 18 of which is bent away from the axis of the shaft. In order to be able to perform an irradiation also of tissue adjacent to the hollow shaft, a rigid holding tube 14 for accepting the optical fiber 16, which extends through the hollow shaft 10 in parallel to the optical viewing system 12 and the distal end of which is bent away from the axis of the hollow shaft by a fixed angle of 10° to 110° and positioned fully within the cross section of the hollow shaft. A distance piece 36 which is provided with an irradiation window 32 ensures that the tissue to be irradiated cannot contact the exit location 18 of the optical fiber 16.

We claim:

1. An endoscope, especially for urological applications, comprising a hollow shaft, an optical viewing system which has a fiber optical source of illumination and which is positioned inside the hollow shaft, and an optical fiber which is positioned inside the hollow shaft together with the optical viewing system, which is connected to an external laser light source at its proximal end and the distal end of which is bent away from the axis of the shaft, characterized by a rigid holding tube accepting the optical fiber, which extends through the hollow shaft in parallel to the optical viewing system and the distal end of which is bent away from the axis of the hollow shaft by a fixed angle of 10° C. to 110° C. and positioned fullly within the cross section of the hollow shaft, the holding tube having a jacket slit for laterally inserting the end of the optical fiber at least in the region of its bent distal end.

2. The endoscope of claim 1, characterized in that the optical fiber protrudes with its free distal end over the free end of the holding tube within the cross section of the hollow shaft.

3. The endoscope of claim 1, characterized in that the jacket slit is open toward the free end of the holding tube.

4. The endoscope of claim 1 or 3, characterized in that the jacket slit extends parallel to the axis from the distal end over a distance in the straight part of the holding tube.

5. The endoscope of claim 1, characterized in that the jacket slit is open in the proximal direction at least in the vicinity of the free bent end of the holding tube.

6. The endoscope of claim 1, characterized in that the jacket slit extends toward the free end of the holding tube in a helical manner such that it is open in the distal and/or lateral direction in the region of the root of the bend and in the proximal direction in the vicinity of the free end.

7. The endoscope of claim 6, characterized in that the part of the holding tube which has a closed jacket and is aligned axially has an axial passage opening for the optical fiber, the passage opening being formed by the helical and laterally bent jacket slit.

8. The endoscope of claim 1, characterized in that the jacket slit extends straight past the bend toward the free distal end.

9. The endoscope of claim 1, characterized in that the holding tube incorporates a clamping member which pushes the optical fiber into the jacket slit and also bends the end of the optical fiber.

10. The endoscope of claim 9, characterized in that the clamping member has a clamping shell which is bent at its distal end, movable on the holding tube in an axially parallel direction, and which has a slit opening which is complementary to the jacket slit of the holding tube or which overlaps or projects into the jacket slit.

11. The endoscope of claim 9 or 10, characterized in that the clamping member is engageable in the holding tube in its end position.

12. The endoscope of claim 1, characterized in that the holding tube has a closed ring which delimits the jacket slit at the free end of the holding tube.

13. The endoscope of claim 1, characterized in that the holding tube is aligned parallel with respect to the optical viewing system within the hollow shaft and is bent toward the optical path of the optical viewing system at its distal end.

14. The endoscope of claim 1, characterized in that the optical viewing system has an observation angle which is directed slanted with respect to the axis of the shaft in the direction of the area of irradiation.

15. The endoscope of claim 14, characterized in that the angle of bending of the holding tube and of the optical fiber with respect to the axis of the shaft is two to nine times greater than the angle of observation of the optical viewing system.

16. The endoscope of claim 1, characterized in that the hollow shaft has an oval cross section and that the axes of the optical viewing system and of the holding tube penetrate the long principal axis of the oval cross section of the hollow shaft.

17. The endoscope of claim 16, characterized in that the optical viewing system is positioned generally in the center of the hollow shaft and that the holding tube is positioned eccentrically and non-rotatably in the hollow shaft.

18. The endoscope of claim 1, characterized in that the hollow shaft has an opening in the vicinity of its distal end, which is open in the direction of the bend of the holding tube, which extends to the distal end and which is limited by a beak-like shaft tip.

19. The endoscope of claim 1, characterized in that the free bent end of the holding tube is laterally enclosed by a distance piece.

20. The endoscope of claim 19, characterized in that the distance piece is simultaneously formed to be a window defining the area of irradiation.

21. The endoscope of claim 20, characterized in that the distance piece has a wire loop which forms the window.

22. The endoscope of claim 21, characterized in that the wire loop is positioned within the opening in the hollow shaft and is preferably rigidly connected to the hollow shaft.

23. The endoscope of claim 22, characterized in that the distal end of the wire loop is bent against and affixed to the distal end of the shaft in a clip-like manner.

24. The endoscope of claim 1, characterized in that the holding tube consists of a pliable nickel-titanium alloy.

25. The endoscope of claim 1, characterized in that the radius of bending of the holding tube is one quarter to one half of the average diameter of the shaft.

26. The endoscope of claims 1, characterized in that the holding tube is movable to-and-fro in a limited way relative to the optical viewing system in the direction of the axis of the hollow shaft by means of a proximal actuating mechanism.

27. The endoscope of claim 26, characterized in that the actuating mechanism has a holder which carries the optical viewing system and is removably connected to the proximal end of the hollow shaft and a slider which is movable relative to the holder parallel to the axis of the hollow shaft against the force of a spring and carries the holding tube.

28. The endoscope of claim 27, characterized in that the holder has an axial guide for the holding tube, which is formed by a guide jaw which is connected to the holder and which carries the optical viewing system and by a guide jaw which is separated from the holding tube in an axial parting plane of the holding tube and movable in a limited way along the holder transverse to the parting plane.

29. The endoscope of claim 28, characterized in that the guide jaws have partially conical shoulders which complement each other to form a closed outer cone, are insertable into an inner cone of the hollow shaft, are clampable in this preferably by way of a bayonet catch in a fluid-tight manner, and can be pressed against each other at their parting plane.

30. The endoscope of claim 27, characterized in that the optical viewing system has an optical tube which is rigidly coupled to the holder, an axial guide for the holding tube being positioned at the enclosing surface of the optical tube.

31. The endoscope of claim 30, characterized in that the holding tube is laterally engageable into the radially open-edged axial guide.

32. The endoscope of claims 27, characterized in that the holding tube has a radially protruding adjusting member rigidly positioned at its proximal end, and that the slider has an axially continuous, radially accessible slotted receiving means for the holding tube, the slotted receiving means having a pocket which retains the adjusting member in an axially form-fitting manner.

33. The endoscope of claim 32, characterized in that the adjusting member is limitedly pivotable in the pocket together with the holding tube about the axis of the holding tube by way of a positioning mechanism which is positioned on the slider.

34. The endoscope of claim 27, characterized in that the holding tube is replaceable with a holding tube for an optical fiber, the holding tube having a distal cannular bevel, and that there is provided a holder-connected locking member which acts on the proximal end of the optical fiber.

35. An endoscope, especially for urological applications, comprising a hollow shaft, an optical viewing system which has a fiber optical source of illumination and which is positioned inside the hollow shaft, and an optical fiber which is preferably positioned inside the hollow shaft together with the optical viewing system, which is connected to an external laser light source at its proximal end and the distal end of which is bent away from the axis of the shaft, characterized by a rigid holding tube accepting the optical fiber, which extends through the hollow shaft in parallel to the optical viewing system and the distal end of which is bent away from the axis of the hollow shaft by a fixed angle of 10° C. to 110° C. and positioned fully within the cross section of the hollow shaft, the optical fiber, which protrudes over the proximal end of the holding tube, being removably connectable to a mother fiber which leads to the laser light source by way of a plug-type connector.

* * * * *